United States Patent
Gabriel et al.

[19]

[11] Patent Number: 5,556,433
[45] Date of Patent: Sep. 17, 1996

[54] MODULAR KNEE PROSTHESIS

[75] Inventors: Stefan M. Gabriel, Lakeville; David G. Sheehan, Carver, both of Mass.

[73] Assignee: Johnson & Johnson Professional, Inc., Raynham, Mass.

[21] Appl. No.: 347,828

[22] Filed: Dec. 1, 1994

[51] Int. Cl.$^6$ ..................................................... A61F 2/38
[52] U.S. Cl. ................................................. 623/20; 623/18
[58] Field of Search ............................. 623/18, 20; 411/398

[56] References Cited

U.S. PATENT DOCUMENTS

| | | |
|---|---|---|
| 4,822,366 | 4/1989 | Bolesky ................................. 623/20 |
| 4,904,110 | 2/1990 | Klein ..................................... 411/398 |
| 4,985,037 | 1/1991 | Petersen ................................. 623/20 |
| 5,127,914 | 7/1992 | Calderale et a. ....................... 606/65 |
| 5,133,760 | 7/1992 | Petersen et al. ........................ 623/20 |
| 5,152,796 | 10/1992 | Slamin .................................. 623/20 |
| 5,290,313 | 3/1994 | Heldreth ................................. 623/20 |
| 5,326,359 | 7/1994 | Oudard .................................. 623/20 |
| 5,336,225 | 8/1994 | Zang ..................................... 411/398 |

FOREIGN PATENT DOCUMENTS

| | | |
|---|---|---|
| 0531263A1 | 3/1993 | European Pat. Off. . |
| 0529408 | 3/1993 | European Pat. Off. .................. 623/20 |
| 0473375 | 3/1929 | Germany ............................... 411/398 |

OTHER PUBLICATIONS

Johnson & Johnson Orthopaedics Research & Development "*P.F.C.®Modular Knee System Research Data and Laboratory Testing*", cover and pp. 8, 36 and 37 (1989).

*Primary Examiner*—David H. Willse
*Assistant Examiner*—Bruce E. Snow
*Attorney, Agent, or Firm*—Nutter, McClennen & Fish, LLP; William C. Geary, III

[57] ABSTRACT

A modular knee prosthesis includes a femoral component having a pair of spaced apart condylar portions each having a superior articulating surface and an inferior surface, and a boss structure disposed between and connecting the condylar portions. The prosthesis further includes an elongate stem member that mounts within the medullary canal of a distal portion of a femur, a collar and at least one securing bolt. The collar mounts upon the external end of the stem member, and has a distal surface that is substantially transverse to a longitudinal axis of the stem member when mounted thereon. The collar distal surface and the inferior surface of the boss structure define a selected mounting angle therebetween, and the securing bolt, which is adapted to mount within an aperture formed in the boss structure, has a head portion with a spherical first surface from which an elongate shaft portion extends. The shaft of the securing bolt can be disposed at a generally centrally located position or at a non-centrally located position on the head portion of the bolt.

22 Claims, 6 Drawing Sheets

MODULAR KNEE PROSTHESIS

BACKGROUND OF THE INVENTION

This invention relates to joint prosthesis, and more particularly to modular knee joint prostheses employed during knee arthroplasty procedures.

Knee arthroplasty is a well known surgical procedure by which a diseased and/or damaged natural knee joint is replaced by a prosthetic knee joint. Typical knee prostheses include a tibial component, a femoral component, and a patellar component. The femoral component generally includes a pair of spaced apart condylar portions, the superior surfaces of which articulate with a portion of the tibial component. A femoral stem assembly can also be used to provide lateral stability to the replaced knee joint. Femoral stem assemblies often include a stem member which seats within the medullary canal of a distal portion of a femur. The stem is typically coupled to the femoral component by a specialized collar and bolt.

Knee joint prostheses are available as modular assemblies to reduce the number of individual components that must be purchased and stocked, and to reduce the associated component handling time by the surgeon during arthroplasty procedures. An example of a prior art modular knee prosthesis is described in U.S. Pat. No. 5,152,796 (Slamin). The Slamin patent describes a modular knee prosthesis that includes a femoral component and a series of bolts that attach to and extend from the femoral component at different angles corresponding to different valgus angles. The valgus angle is defined as the angle between the center line of the femur and the vertical axis connecting the distal femur and the center of the femoral head, and is typically between 5° and 9°. The prosthesis also includes a plurality of femoral stems having different lengths and diameters.

Despite existing modular knee joint prostheses, there remains a need for a modular knee joint prosthesis that has sufficient versatility to accommodate differing patient anatomy and joint conditions. Many modern modular knee prostheses are characterized by a relatively excessive number of components with little or no part interchangeability. Such systems tend to increase purchasing costs because of part waste. Additionally, the excessive number of parts must be handled and stocked, thus increasing costs associated with inventory control and management.

It is thus an object of the invention to provide a modular knee prosthesis having sufficient versatility to accommodate different patient anatomy and joint conditions while maintaining a relatively low component count. It is another object of the invention to provide a modular knee prosthesis having components that are physiologically and geometrically compatible with different anatomical conditions. Still another object of the invention is to provide a modular knee prosthesis that is suitable for use in both right and left knee procedures. Other general and more specific objects of the invention will in part be apparent from the drawings and description which follow.

SUMMARY OF THE INVENTION

The present invention relates to a modular knee joint prosthesis having improved versatility while reducing the overall component count. Components of the modular prosthesis of the invention are able to be used with both right and left side prostheses.

The modular knee prosthesis of the invention includes a femoral component having a pair of spaced apart condylar portions each having a superior, articulation surface and an inferior surface. A boss structure is present on the femoral component and is disposed between and connects the condylar portions. The boss structure has an inferior surface that extends, in a first orientation, generally horizontally, in a transverse plane, and an opposed superior surface which has an aperture of a selected configuration. The modular knee prosthesis of the invention further includes an elongate stem member that mounts within the medullary canal of a distal portion of a femur. The stem member preferably has an open, distal end that is adjacent to the femoral component.

The modular knee prosthesis also includes a collar and at least one securing bolt. The collar mounts on the external end of the stem member, and has a distal surface that is substantially transverse to a longitudinal axis of the stem member when mounted thereon. According to one practice of the invention, the collar distal surface and the inferior surface of the boss structure define a selected mounting angle therebetween that is preferably between about 0 and 9 degrees.

The securing bolt, which is adapted to mount within the aperture of the boss structure, has a head portion with a spherical boss-engaging surface from which an elongate shaft portion extends. In one embodiment, the shaft of the securing bolt is disposed at and extends from a generally centrally located position of the bolt head portion. In an alternate embodiment, the shaft portion of the bolt is disposed at and extends from a non-centrally located position of the head portion, such that the shaft is offset from center. Advantageously, providing a modular knee prosthesis with a single stem and with at least two collars having different mounting angles and offset and non-offset securing bolts reduces the number of necessary prosthetic components, while providing a modular knee prosthesis that has improved versatility and which is suitable for use, without modification, in both left and right prostheses.

According to another practice of the invention, the securing bolt seats within and engages the aperture of the boss structure. More specifically, the superior articulating surface of the boss structure preferably includes a cavity that ends in a spherical endwall that houses the boss aperture. The mating engagement of the spherical surface of the bolt head and the spherical endwall of the cavity allows the bolt to be positioned within the aperture at a selected angle relative to the transverse plane. The exact angle at which the bolt shaft portion extends from the inferior surface of the boss structure is determined by the collar mounting angle. According to one aspect, the aperture formed within the boss structure has a selected shape and can be elongated in either the anterior-posterior direction or medial-lateral direction.

According to a further aspect of the invention, the head portion of the bolt includes a first anti-rotation element for preventing unwanted rotation of the bolt when the bolt is mounted within the boss aperture. Additionally, the boss structure includes a second anti-rotation element, which engages the first anti-rotation element of the bolt, for preventing rotation of the bolt when mounted within the boss aperture. In one embodiment, the second anti-rotation element is formed on the superior surface of the boss structure.

A third anti-rotation element may be associated with the collar for preventing rotation of the collar when mounted on the inferior surface of the boss structure. The inferior surface of the boss structure preferably includes a fourth anti-rotation element, which engages the third anti-rotation element of the collar, for preventing rotation of the collar when mounted on the boss structure. The fourth anti-rotation element is preferably formed on the inferior surface of the boss structure.

The modular knee prosthesis of the invention can include a locking element, e.g., a snap-ring, that secures the collar to the elongated stem member. The locking element is preferably disposed in an interference fit with the collar and stem. In a preferred embodiment, the elongate stem member is rotatable about its longitudinal axis independently of the collar.

BRIEF DESCRIPTION OF THE DRAWINGS

The foregoing and other objects, features and advantages of the invention will be apparent from the following description and the accompanying drawings, in which like reference characters refer to the same parts throughout the different views.

DETAILED DESCRIPTION OF THE INVENTION

Figure 1:
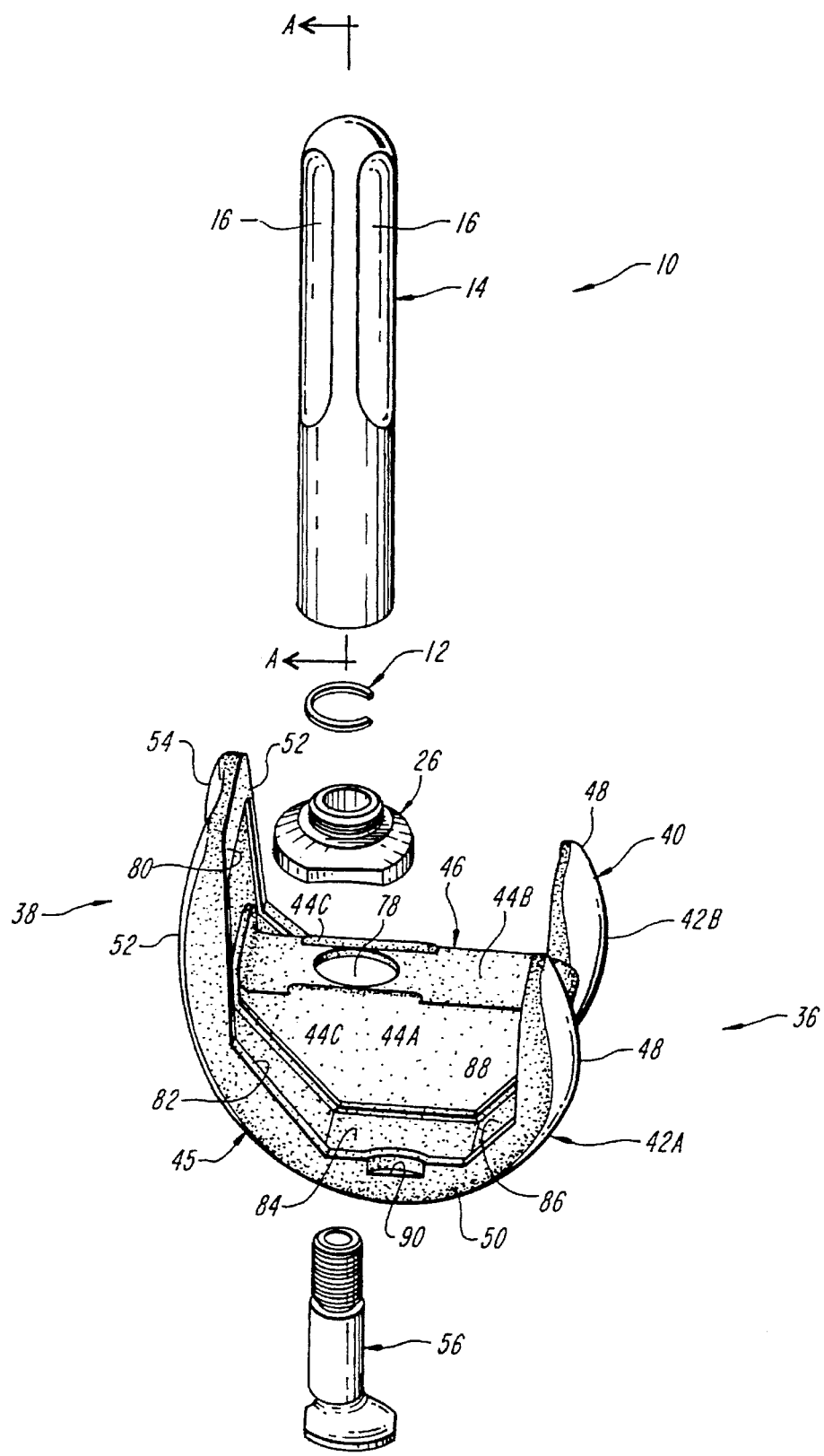
FIG. 1 is an unassembled perspective view of a modular knee prosthesis according to the present invention that includes a right knee femoral component, but that is generally designed for use in both right and left knees.

As illustrated in FIG. 1, the modular knee prosthesis 10 of the invention includes a femoral stem 14, a collar 26, a femoral component 40, and a securing bolt 56. The knee prosthesis 10 can further include a snap-ring 12, similar in type and operation to that described in U.S. Pat. No. 5,152,796, which is herein incorporated by reference. The illustrated modular knee prosthesis 10, except the illustrated femoral component, is suitable for use, without modification, as either a left or a right knee prosthesis.

Figure 2A:
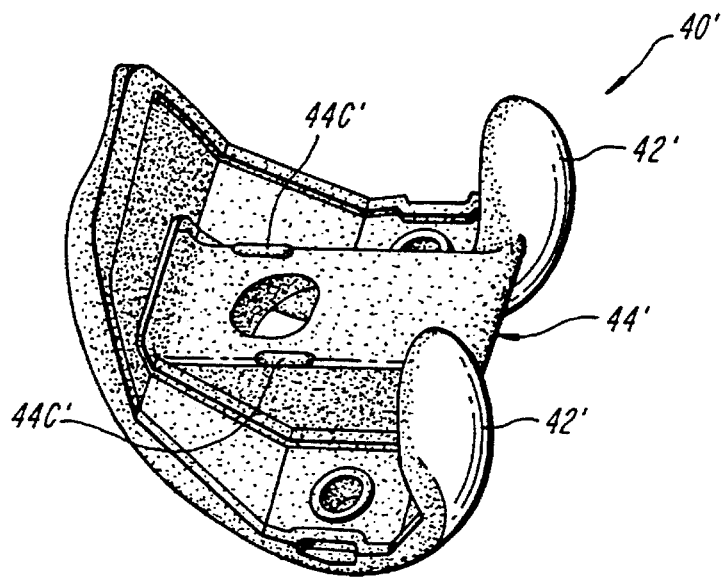
FIG. 2A is a perspective view of one embodiment of a femoral component for use with the right knee and for use with the modular knee prosthesis of FIG. 1.
Figure 2B:
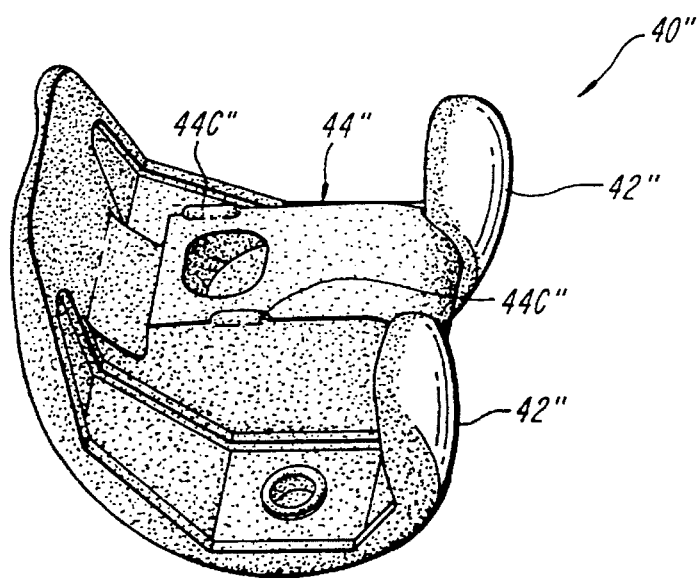
FIG. 2B is a perspective view of another embodiment of a femoral component useful with the modular prosthesis of FIG. 1, and that is designed for use in both right and left knees.
Figure 3:
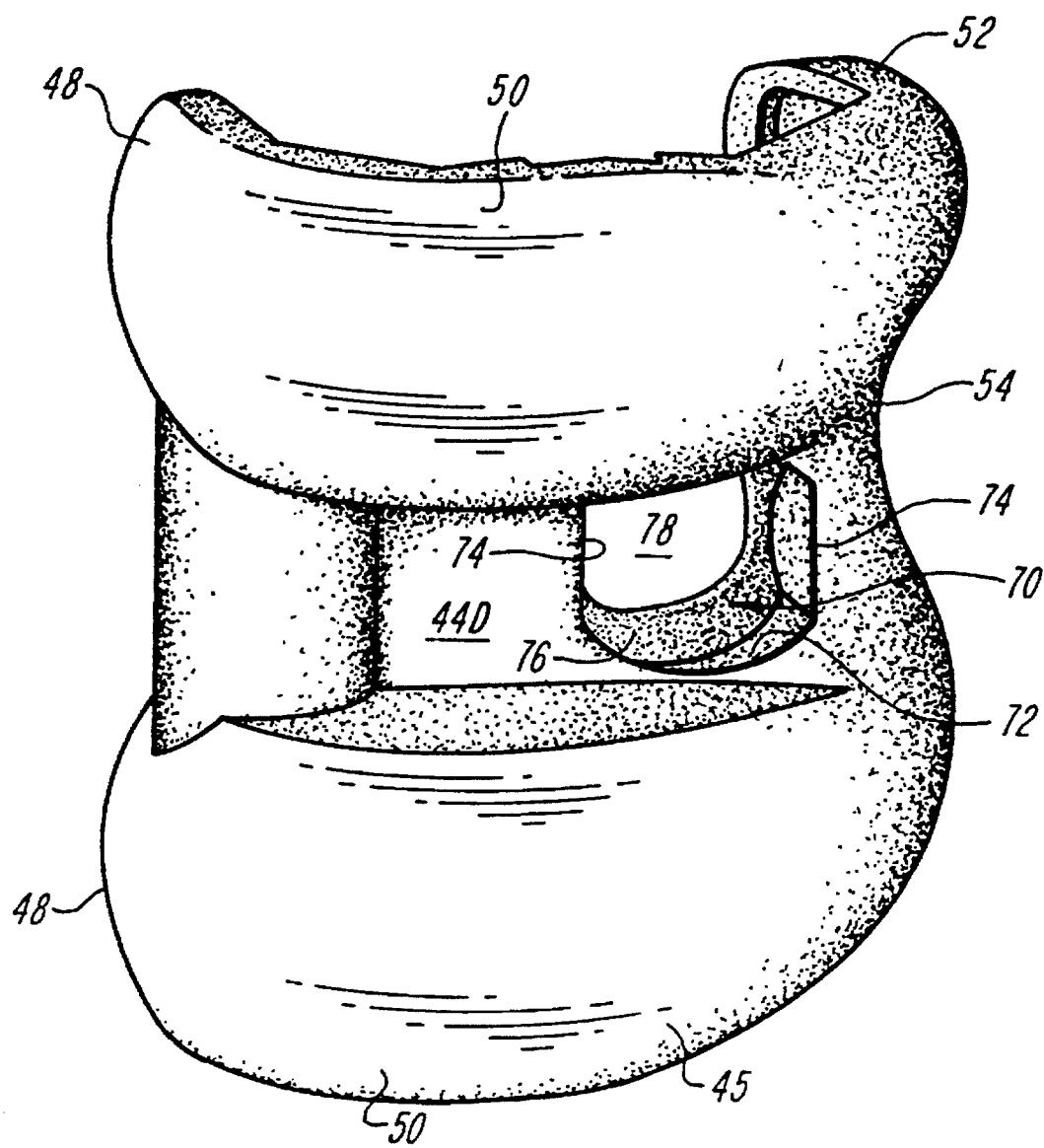
FIG. 3 is a bottom view of the femoral component of FIG. 1.

Referring to FIGS. 1 through 3, the femoral component 40 has a pair of condylar portions 42A, 42B that are connected by an intercondylar region or boss 44. The femoral component 40 has a superior articulation surface 45 and an opposed inferior surface 46. Further, the femoral component 40 has a posterior side 36 and an anterior side 38. The anterior side 38 of the femoral component 40 includes a patellar groove 54, shown in FIG. 3, within which seats a patellar prosthetic component (not shown). The superior surfaces 45 of the curved condylar portions 42A, 42B articulate with a prosthetic tibial component (not shown) mounted on the head of the tibia, in a manner well known to those of ordinary skill in the art.

The boss structure 44 has a pair of substantially vertical side walls 44A that are generally orthogonal to a top, inferior surface 44B. The top surface 44B preferably has formed thereon a pair of raised ridges 44C that constitute a collar anti-rotation element, as described in further detail below.

With reference to FIGS. 1 and 3, the boss 44 further has a cavity 70 formed within a bottom superior surface 44D. An aperture 78 disposed within the cavity 70 extends between the superior and inferior surfaces 45, 46, respectively, of the boss structure 44 and has a selected shape such that it can be elongated either in the anterior-posterior direction or the medial-lateral direction. Preferably, aperture 78 is elongated in the anterior-posterior direction. The shape of the aperture can be elliptical, oval, spherical, or of any other suitable shape that allows a sufficient amount of translation of the securing bolt shaft when the bolt is mounted within the aperture.

The transverse plane is defined as the horizontal plane that extends through the knee of an upright subject and that is orthogonal to both the coronal plane and the sagittal plane, as will be appreciated by those having ordinary skill in the art.

The cavity 70 preferably has a pair of arcuate medial and lateral side walls 72, and a pair of substantially flat anterior and posterior side walls 74 that form a bolt anti-rotation mechanism, as described in further detail below. The cavity further includes an endwall 76 that has a substantially spherical or rounded shape for seating a correspondingly shaped head of the securing bolt 56.

The inferior surface 46 of the condylar portions 42A, 42B forms a series of integral surfaces that extend between the anterior and posterior sides of the femoral component. Referring to FIG. 1, the inferior surface of each condylar portion 42 comprises an anterior vertical surface 80, an axially spaced and downwardly extending canted surface 82, a substantially horizontal surface 84, an axially spaced and upwardly extending canted surface 86, and a posterior vertical surface 88. The horizontal surface 84 of each condylar portion has an indentation 90 that extends partly into the inferior surface of each condylar portion. The indentation allows the surgeon to grasp and handle the femoral component via a suitable handling instrument.

The femoral component 40 and boss 44 can have a variety of shapes, as shown in FIGS. 2A and 2B. Elements of the femoral component 40' which are common to the elements of the femoral component of FIGS. 1 and 3 are designated with like reference numerals with a superscript prime for FIG. 2A components, and with a superscript double prime for FIG. 2B components. The femoral component 40' of FIG. 2A has a boss structure 44' that has a second selected shape. Additionally, the illustrated raised ridges 44C' forming the collar anti-rotation mechanism are axially offset relative to each other. With reference to FIG. 2B, the boss structure 44" of the illustrated femoral component 40" has a third preferred shape. The raised ridges 44C" of the boss structure are also axially offset, similar to those of FIG. 2A. Those of ordinary skill will readily recognize that other shapes of the femoral component 40, boss structure 44 and condylar portions 42 exist.

Figure 4A:
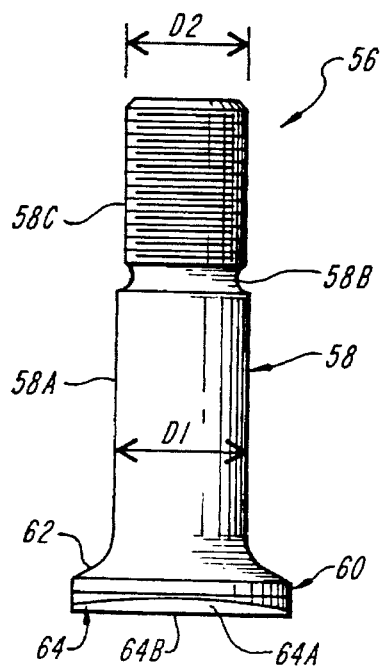
FIG. 4A is a side view of one embodiment of a securing bolt useful with the modular knee prosthesis of FIG. 1.

FIGS. 4A–5B illustrate preferred embodiments of the securing bolt of FIG. 1. With reference to FIG. 4A, the bolt 56 of the first embodiment has a shaft portion 58 that extends upwardly and outwardly from a bolt head 60. The shaft has a lower unthreaded portion 58A that has an outer diameter (D1) less than the outer diameter of bolt head 60, and an upper, threaded portion 58C that is integral with the lower unthreaded portion 58A. Preferably, an indented neck portion 58B separates the upper and lower portions 58C, 58A of bolt 56. The outer diameter (D2) of the upper portion 58C is preferably slightly less than the outer diameter (D1) of the lower shaft portion 58A.

The bolt head portion 60 has a boss aperture-engaging surface 62, and an opposed, top surface 64 that includes a pair of canted surfaces 64A that join at an apex 64B. The aperture-engaging surface 62 preferably has a rounded or spherical shape complementary to that of the endwall 76 of the boss cavity 70. The mating engagement of the aperture-engaging surface 62 of the bolt head 60 and the shaped endwall 76 of the boss cavity 70 preferably positions the bolt shaft within the aperture. The bolt shaft 58 extends from the boss top surface 44B at a selected angle determined by the shape of the aperture 78 and by the mounting angle of the collar 26. The shape of the aperture 78 helps determine the allowable angle range of the bolt shaft by allowing the bolt shaft to translate within the confines of the aperture, and to eventually seat at a selected position therein, as described in further detail below. Although the endwall 76 and aperture-engaging surface 62 are shown with spherically-shaped contours, those of ordinary skill will recognize that other compatible configurations are possible.

Figure 4B:
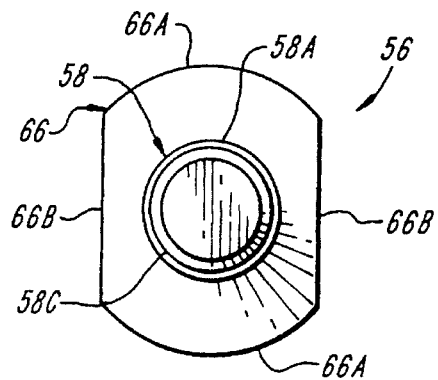
FIG. 4B is a top view of the securing bolt of FIG. 4A.

As illustrated in FIG. 4B, the top surface 64 of the bolt head 60 has a peripheral surface 66 that is defined by a pair of opposed, arcuate sides 66A and a pair of opposed, substantially flat sides 66B. The flat sides 66B matingly engage the flat side walls 74 of the boss cavity 70 and cooperate therewith to secure the bolt within the cavity and to prevent unwanted rotation of the bolt when secured therein.

With further reference to FIG. 4B, in one embodiment the bolt is constructed such that the shaft portion 58 of the bolt extends from a generally centrally located position on the bolt head 60. This arrangement allows the bolt shaft to extend from the inferior surface of the femoral component when the bolt is mounted within the boss aperture at a selected location and desired angle relative to the inferior surface 46.

Figure 5A:
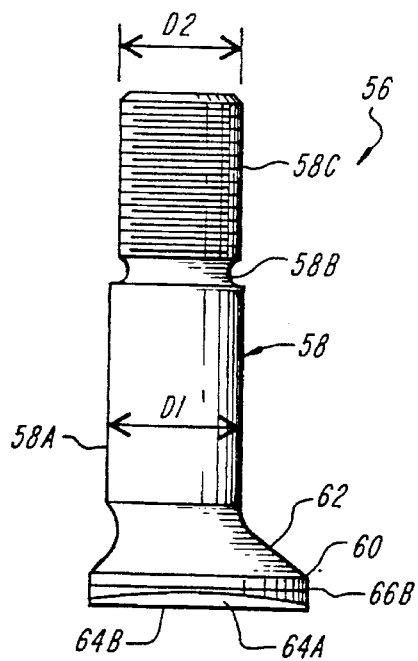
FIG. 5A is a side view of an alternate embodiment of a securing bolt useful with the modular knee prosthesis of FIG. 1.
Figure 5B:
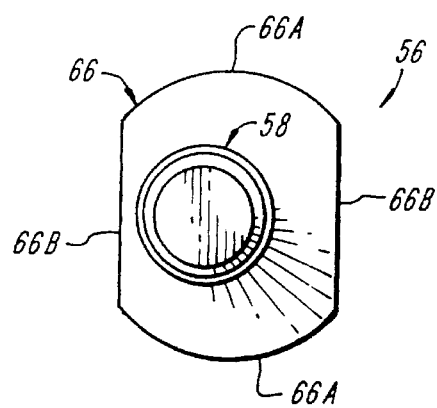
FIG. 5B is a top view, from the shaft, of the securing bolt of FIG. 5A.

FIGS. 5A and 5B illustrate another embodiment of a securing bolt 56 constructed according to the invention. In this embodiment, bolt 56 is similar to that described above and shown in FIGS. 4A and 4B, except that the shaft 58 is positioned on the bolt head 60 in an offset, non-centered position. As illustrated, the shaft portion 58 of the bolt extends upwardly from a position axially offset a selected distance from a generally centrally located position of the bolt head 60. The distance by which the shaft is offset from this generally centrally located position is in the range of about 0 mm to about 5 mm. Preferably, the offset distance is about 2 mm.

This offset construction of the bolt 56 allows the bolt shaft 58 to extend from the boss inferior surface 46, when the bolt is mounted within the boss aperture, at a selected angle and axial orientation relative to the inferior surface 46 of the femoral component 40. For example, an offset bolt (FIGS. 5A and 5B) oriented in either an anterior or posterior direction may be necessary for differing anatomies, or where bony deficiencies exist in certain areas of the femur.

The illustrated bolt of FIGS. 4A and 4B can be used in both left or right side prostheses where no bolt offset is desired, for example, for differing anatomies or where bony deficiencies exist in certain areas of the femur. Likewise, the offset bolt illustrated in FIGS. 5A and 5B can be used in both right and left side prostheses where an anterior or posterior, or medial or lateral offset is needed.

Figure 6A:
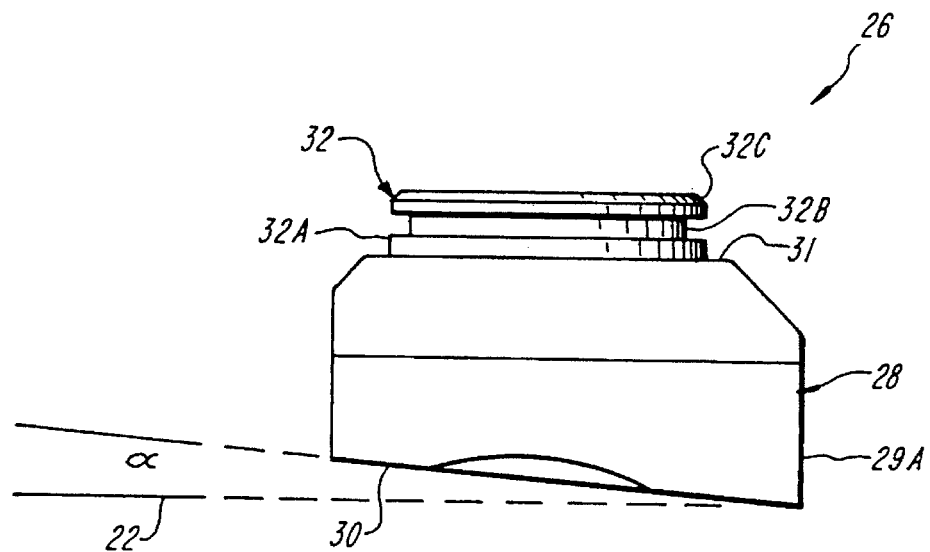
FIG. 6A is a side view of a collar useful with the modular knee prosthesis of FIG. 1.
Figure 6B:
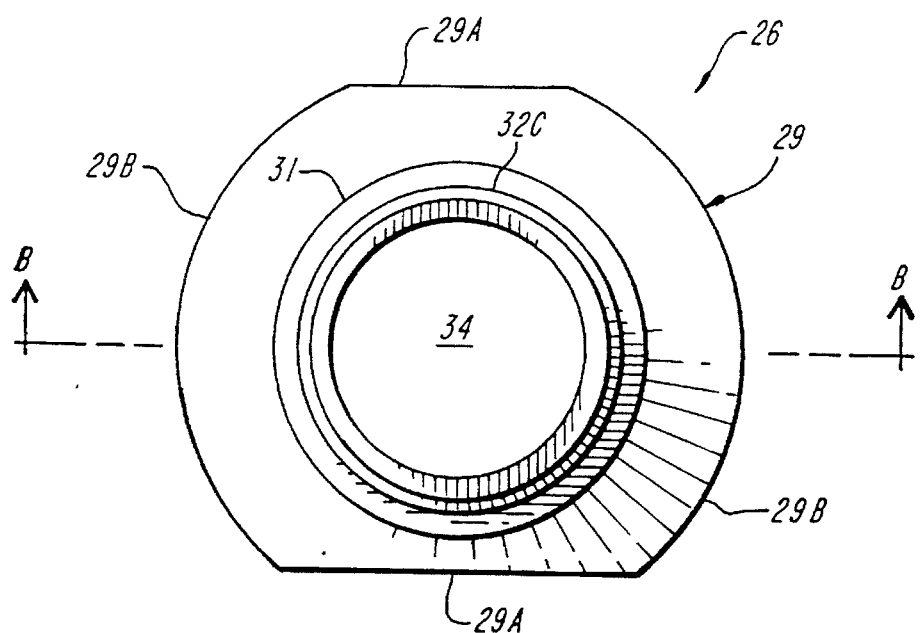
FIG. 6B is a top view of the collar of FIG. 6A.

With reference to FIGS. 6A and 6B, the collar 26 has a central body portion 28 that has an outer peripheral surface 29 and a boss engaging surface 30. The collar further includes a neck portion 32 that extends upwardly from a stem-seating surface 31. The neck 32 preferably includes a first annular portion 32A and a stepped annular portion 32B. A lip 32C formed along the top of the second stepped annular surface 32B overhangs the first stepped surface 32A. The distal end of the stem 14, when assembled with the collar, preferably engages the stem-seating surface 31, which is sized to receive femoral stems having various diameters, including diameters of about 13 mm and about 15 mm.

The boss engaging surface 30 is preferably canted and forms an angle with the transverse plane 22. The engaging surface 30 and the top, inferior surface 46 of the boss 44, which lies in the transverse plane, form a mounting angle ($\alpha$) when the collar is assembled with the femoral component and engages the boss top surface. The angle ($\alpha$) is preferably between about 0° and about 15°. According to one practice of the invention, the boss engaging surface 30 can be canted in the anterior-posterior direction to either the anterior or posterior side as measured in the sagittal plane. Likewise, the surface 30 can be canted in the medial-lateral direction to either the medial side or the posterior side as measured in the coronal plane. Preferably, the angle ($\alpha$) can range between about 0° and about 15° in any direction. This varied collar angulation provides a plurality of stem mounting angles which is compatible with the various possible orientations of the femoral stem when mounted within the distal portion of the femur. Those of ordinary skill in the art readily appreciate that the boss mounting surface 30 can be configured to provide any combination of coronal and sagittal plane angulations that are constrained by the foregoing angle ranges.

The collar 26 can be used with either right or left side knee prostheses. Generally, the collar is positioned such that the angle ($\alpha$) is to the lateral side of the prosthesis, as measured in the coronal plane. The same collar can be used in either a left or right side prosthesis by simply reversing the orientation of the collar on the prosthesis to ensure a lateral angle for the femoral stem 14.

With reference to FIG. 6B, the collar peripheral surface 29 has a pair of opposed arcuate sides 29B and a pair of opposed, flat sides 29A. Flat sides 29A are adapted to engage the raised ridges 44C of the boss top surface 44B. The mating contact between the raised ridges 44C and the flat sides 29A of the collar peripheral surface prevents unwanted rotation of the collar when mounted on the boss top surface 44B.

Figure 6C:
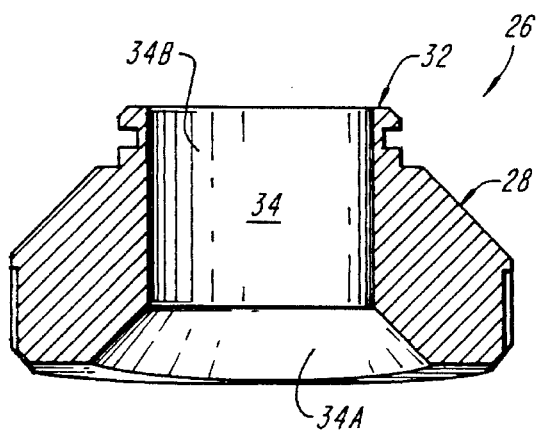
FIG. 6C is a cross-sectional view of the collar of FIG. 6A taken along line B—B of FIG. 6B.

As illustrated in FIG. 6C, the collar 26 further has a central aperture 34 which seats the bolt shaft 58. The aperture 34 has a funnel-like portion 34A adjacent the boss mounting surface 30, and a cylindrical portion 34B that extends upwardly from the funnel-like portion 34A to the neck 32 of the collar. The funnel-like portion 34A provides an additional clearance space for bolt insertion.

Figure 7:
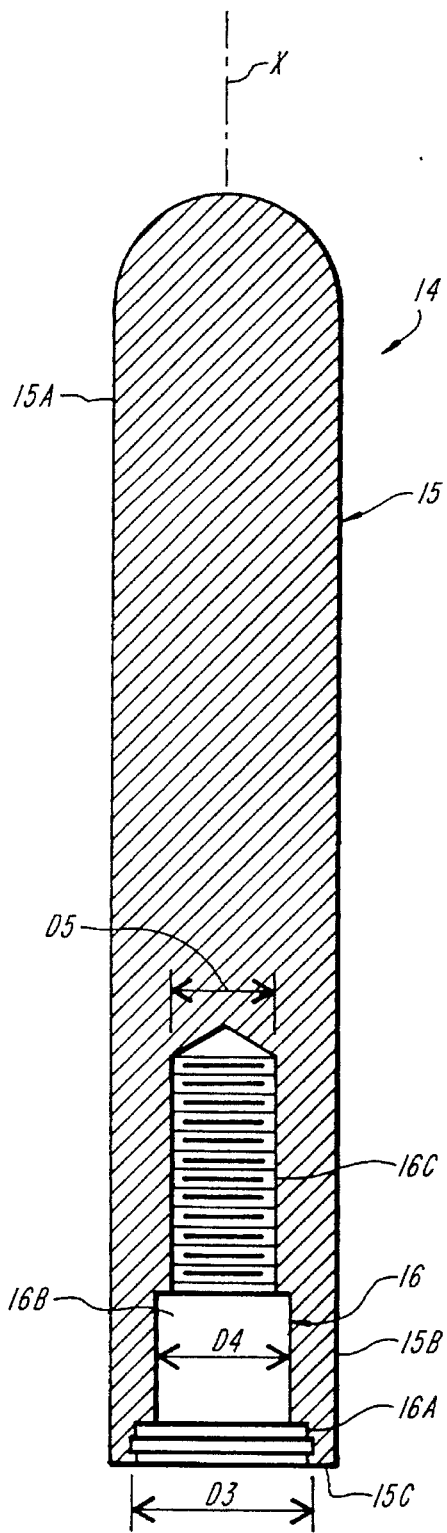
FIG. 7 is a cross-sectional view of the femoral stem of FIG. 1 along line

Referring to FIGS. 1 and 7, the femoral stem 14 has an elongate body 15 that extends along a longitudinal axis (x).

A series of spaced flutes 16 are formed along a proximal portion 15A of the body 15, FIG. 1. The flutes 16 inhibit rotation of the stem within the medullary canal of the femur. The bottom portion 15B, e.g., distal end, of the stem body 15 further has a collar and bolt-receiving aperture 16 formed therein. The aperture 16 formed in the stem bottom surface 15C has a first aperture portion 16A having an outer diameter (D3) that is slightly larger that the outer diameter of the first annular surface 32A of the collar, FIG. 5A, thereby allowing the collar neck to mount within the stem aperture 16. The aperture 16 has a second axially spaced portion 16B that has a diameter (D4) that is smaller than diameter (D3) but slightly larger than the diameter (D1) of the bolt shaft 58, FIG. 6A. The aperture further includes an axially spaced, threaded third portion 16C having an outer diameter (D5) that is less than the diameter (D1), but larger than the diameter (D2) of the bolt shaft. This axial successive configuration of the aperture 16 receives the axially spaced portions of the bolt shaft 58A–58C, and allows the bolt threaded portion 58C to threadingly engage with the threaded aperture portion 16C. The outer diameter of the stem bottom portion preferably ranges between about 10 mm and about 20 mm, and most preferably between about 10.5 mm and about 15 mm. The illustrated stem 14 is suitable for use, without modification, in both left and right side prostheses.

When assembled, the collar 26 is mounted on the top surface 46, e.g., inferior surface, of the boss 44, and the flat sides 66B of the collar are aligned with the raised ridges 44C. The raised ridges prevent unwanted rotation of the collar when mounted thereon. The distal end of the femoral stem is then placed over the neck 32 of the collar 26. In this assembly, the neck portion 32 seats within the first portion 16A of the stem aperture 16, but is not rigidly captured therein. Thus, the stem is rotatable about the stem axis (x) independent of the collar, since the raised ridges of the boss prevent the collar from rotating.

The securing bolt 56 is then inserted into the boss cavity 70 from the underside of the boss and through the boss aperture 78, such that the bolt shaft extends upwardly from the boss top surface. The spherical engaging surface 62 of the bolt head 60 mates with and engages the similarly configured endwall 76 of the cavity. The selected shape of the cavity endwall allows the bolt shaft to seat within the cavity at an angle that is determined by the collar 26.

The boss mounting surface 30 of the collar 26 determines the stem angulation and the position at which the bolt shaft protrudes into and extends from the collar 26. The threaded portion 58C of the bolt shaft 58 threadedly engages the threaded portion 16C of the stem aperture and fixedly secures the stem and collar to the femoral component. In this axially successive assemblage, the collar is pressure fitted between the stem and boss by the threaded engagement of the bolt and stem.

A significant feature of the present invention is the complementary shape of the cavity endwall and the mounting surface of the bolt head, which cooperate to position the bolt at a selected angle determined by the collar mounting angle. The varied positions in which the bolt shaft can be positioned is further facilitated by the selected shape of the aperture, which is preferably elongated in the anterior-posterior direction. Those of ordinary skill in the art will also recognize that the aperture can be elongated in any selected direction in the transverse plane, for example, the medial-lateral direction. In the modular knee prosthesis of the present invention, the bolt shaft of the securing bolt can be centrally located or offset, depending upon the surgeon's needs. Additionally, since the collar is pressure fitted between the stem and bolt, the stem and collar can be separately provided in a packaged modular knee prosthesis. For example, the packaged modular knee prosthesis can include a femoral component, an offset and/or a non offset type bolt, a collar or collars having a 5 degree and/or a 7 degree canted mounting surface, and a femoral stem.

The modular knee prosthesis 10 of the invention can further include a snap-ring 12, FIG. 1, to provide a redundant mechanism for securing the collar to the femoral stem. The illustrated snap-ring 12 preferably mounts in a circumferential slot formed by the second annular surface 32B of the collar, FIG. 6A, and a corresponding groove formed along the bottom portion of the stem aperture (not shown). The snap-ring seats partially within the circumferential slot within the collar and within the groove formed in the stem, thereby locking the stem onto the collar.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements concerning of the scope of the invention which, as a matter of language, might be said to fall therebetween.

What is claimed is:

1. A modular knee prosthesis comprising a femoral component having a pair of spaced apart condylar portions each having a superior, articulation surface and an inferior surface, the femoral component further including a boss structure disposed between and connecting the condylar portions, the boss structure having an inferior surface that extends, in a first orientation, generally horizontally in a transverse plane, and an opposed superior surface having a cavity formed therein that terminates in a substantially spherically-shaped endwall, wherein an aperture having an elongated configuration in the transverse plane extends between the inferior and superior surfaces of the boss structure;

an elongate stem member means for mounting within the medullary canal of a distal portion of a femur, the stem member having a closed proximal end and an open distal end;

a collar means for mounting upon the distal end of the stem member, the collar means having a distal surface that is substantially transverse to a longitudinal axis of the stem member when mounted thereon, the collar distal surface and the inferior surface of the boss structure defining a selected mounting angle therebetween; and at least one securing bolt for mounting within the aperture of the boss structure, the securing bolt having a head portion with a spherical first surface from which an elongate shaft portion extends, wherein the engagement between the spherically-shaped endwall of the boss structure and the spherical first surface of the bolt head within the aperture enables mounting at a plurality of mounting angles.

2. The knee prosthesis of claim 1 wherein the shaft portion of the bolt is disposed at and extends from a generally centrally located position on the head portion.

3. The knee prosthesis of claim 1 wherein the shaft portion of the bolt is disposed at and extends from a non-centrally located position on the head portion.

4. The knee prosthesis of claim 3 wherein the elongate shaft portion is offset a selected distance in the transverse plane, in an anterior-posterior direction, from a centrally located position on the bolt head portion.

5. The knee prosthesis of claim 4 wherein the elongate shaft portion of the bolt is offset from the centrally located position of the head portion about 0.1 mm to about 5 mm.

6. The knee prosthesis of claim 1 wherein the distal end of the elongate stem member includes a receiving means for receiving and engaging the shaft portion of the bolt.

7. The knee prosthesis of claim 6 wherein the receiving means includes a cavity, at least a portion of which is threaded.

8. The knee prosthesis of claim 7 wherein at least a portion of the bolt shaft is threaded so as to matingly engage a threaded portion of the cavity.

9. The knee prosthesis of claim 1 wherein the securing bolt is mountable within the collar means such that the spherical first surface of the head portion engages the aperture of the boss, wherein the mounting angle of the collar means determines the angle at which the bolt shaft portion extends from the inferior surface of the boss structure.

10. The knee prosthesis of claim 1 wherein the mounting angle of the distal end of the collar means is in the range of about 0 degrees to about 15 degrees in the medial-lateral direction in the transverse plane, to the medial or lateral side.

11. The knee prosthesis of claim 1 wherein the mounting angle of the distal end of the collar means is in the range of about 0 degrees to about 15 degrees in the anterior-posterior direction in the transverse plane, to the anterior or posterior side.

12. The knee prosthesis of claim 1 wherein the head portion of the bolt includes a first anti-rotation means for preventing rotation of the bolt when mounted within the boss aperture.

13. The knee prosthesis of claim 12 wherein the boss structure further includes a second anti-rotation means for engaging the first anti-rotation means and preventing rotation of the bolt when mounted within the boss aperture, the second anti-rotation means being formed on the superior surface of the boss structure.

14. The knee prosthesis of claim 1 wherein the collar includes a first collar anti-rotation means for preventing rotation of the collar when mounted on the inferior surface of the boss structure.

15. The knee prosthesis of claim 14 wherein the inferior surface of the boss structure includes a second collar anti-rotation means, which engages the first collar anti-rotation means of the collar, for preventing rotation of the collar when mounted on the boss structure, the second collar anti-rotation means being formed on the inferior surface of the boss structure.

16. The knee prosthesis of claim 1 wherein the aperture formed within the inferior surface of the boss structure has a selected shape that is elongated in at least one of an anterior-posterior direction and a medial-lateral direction in the transverse plane.

17. The knee prosthesis of claim 1 further comprising locking means for securing the collar means to the elongated stem member, the locking means being disposed in an interference fit with the collar means and the stem.

18. The knee prosthesis of claim 17 wherein the locking means comprises a snap-ring.

19. The knee prosthesis of claim 1 wherein the elongate stem member is rotatable about its longitudinal axis independent of the collar means.

20. The knee prosthesis of claim 1 wherein the collar means and the elongate stem member are for use, without modification, in right or left side prostheses.

21. The knee prosthesis of claim 2 wherein the securing bolt is for use, without modification, in right or left side prostheses.

22. The knee prosthesis of claim 3 wherein the securing bolt is for use, without modification, in right or left side prostheses.

* * * * *

UNITED STATES PATENT AND TRADEMARK OFFICE
CERTIFICATE OF CORRECTION

PATENT NO. : 5,556,433
DATED : September 17, 1996
INVENTOR(S) : Stefan M. Gabriel and David G. Sheehan It is certified that error appears in the above-indentified patent and that said Letters Patent is hereby corrected as shown below:

Column 1, line 6, prosthesis
should read:
    prostheses

Column 3, line 49,

FIG. 7 is a cross-sectional view of the femoral stem of FIG. 1 along line should read:

FIG. 7 is a cross-sectional view of the femoral stem of FIG. 1 along line A-A.

Signed and Sealed this

Seventeenth Day of June, 1997

Attest:

BRUCE LEHMAN

*Attesting Officer*    *Commissioner of Patents and Trademarks*